United States Patent
Hiroshi

(10) Patent No.: US 8,457,364 B2
(45) Date of Patent: Jun. 4, 2013

(54) CAMERA FOR DETECTING DRIVER'S STATE

(75) Inventor: Nakamura Hiroshi, Chiba (JP)

(73) Assignees: Hyundai Motor Japan R&D Center, Inc., Yokohama (JP); Hyundai Motor Company, Seoul (KR); Kia Motors Corporation, Seoul (KR)

(*) Notice: Subject to any disclaimer, the term of this patent is extended or adjusted under 35 U.S.C. 154(b) by 276 days.

(21) Appl. No.: 13/037,882

(22) Filed: Mar. 1, 2011

(65) Prior Publication Data

US 2012/0087541 A1 Apr. 12, 2012

(30) Foreign Application Priority Data

Oct. 7, 2010 (JP) ................................. 2010-227382

(51) Int. Cl.
*G06K 9/00* (2006.01)

(52) U.S. Cl.
USPC ........... 382/117; 340/575; 340/576; 340/825; 340/573; 340/573.3

(58) Field of Classification Search
USPC .................. 382/117; 340/575, 576, 825, 573, 340/573.3
See application file for complete search history.

(56) References Cited

U.S. PATENT DOCUMENTS 5,682,144 A * 10/1997 Mannik .......................... 340/575
6,559,770 B1 * 5/2003 Zoerb ............................ 340/575

FOREIGN PATENT DOCUMENTS

| JP | 10035320 A | 2/1998 |
| JP | 10086696 A | 4/1998 |
| JP | 2002008020 A | 1/2002 |
| JP | 2003271931 A | 9/2003 |

* cited by examiner

*Primary Examiner* — Mike Rahmjoo
(74) *Attorney, Agent, or Firm* — Edwards Wildman Palmer LLP; Peter F. Corless

(57) ABSTRACT

The present invention provides a camera for detecting a driver's drowsiness state, which can increase the number of pixels in an image of a driver's eye even when using an image sensor having the same number of pixels as a conventional camera instead of a high definition camera. The camera of the present invention is, thus, capable of determining whether the driver's eyes are open or closed. The camera for detecting the driver's state according to the present invention includes a cylindrical lens mounted in front of the camera configured so as to enlarge an image in the vertical direction, a convex lens located in the rear of the cylindrical lens, an image sensor for taking an image of a driver's face formed by the cylindrical lens and the convex lens, and an image processor for extracting an eye area from the image of the driver's face and determining whether the driver's eyes are open or closed.

2 Claims, 3 Drawing Sheets

(A)   (B)

CAMERA FOR DETECTING DRIVER'S STATE

CROSS-REFERENCE TO RELATED APPLICATION

This application claims under 35 U.S.C. §119(a) the benefit of Japanese Patent Application No. 2010-227382 filed Oct. 7, 2010, the entire contents of which are incorporated herein by reference.

BACKGROUND (a) Technical Field

The present invention relates to a camera for detecting a driver's drowsiness. More particularly, it relates to a camera for detecting a driver's state of drowsiness, which can increase the number of pixels in an image of the driver's eyes without using a high definition camera.

(b) Background Art

Japanese Patent Application Publication No. 1998-035320 describes a vehicle condition detector, in which a charge coupled device (CCD) camera, as an image sensor, is mounted in an image pickup part to collect an image of a driver's face. The image of the driver's face is displayed in an enlarged size on a display screen, and an eye area is extracted from the image of the driver's face to determine the state of the driver's drowsiness.

Japanese Patent Application Publication No. 2003-271931 describe an image magnifier, in which an image of a driver's eyes is magnified to determine the driver's drowsiness state. Here, a method for reducing the effect of noise included in an original image (i.e., an image before magnification) is applied to an image after magnification.

In particular, when the image data composed of a plurality of pixels is magnified by the image magnifier, all pixels other than the pixels at an end part in the image data after magnification are generated by interpolation from the plurality of pixel data of the image data before magnification. According to this method, the information of the plurality of pixels before magnification is squeezed into all pixels other than the pixels at the end part in the image after magnification. And, the pixels generated using the pixel data of the image data before magnification, which has noise, are affected by the other pixels, which have no noise. Therefore, the image can be magnified while reducing the effect of the noise present in the image before magnification. However, a considerable amount of time is required to process the image data by software, and, thus, it is not possible to process the image data within a predetermined sampling time.

In the case where the opening and closing of a driver's eyes is detected by a system for detecting a driver's drowsiness state, the pixel data present between the upper and the lower eyelids is as small as 10 pixels in a video graphic array (VGA) camera. As shown in FIG. 4, the resolution of the degree of opening of an eye depends on the number of pixels. Therefore, it may be difficult to determine from the image having a small number of pixels whether the upper and lower eyelids are opened or closed. For example, even when using a high pixel image sensor in which one pixel is increased to four pixels, the brightness of one pixel in the high pixel image sensor is reduced to ¼, and thus the image analysis cannot be simply and easily performed even if the number of pixels increases.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention relates to a camera for detecting a driver's drowsiness. In particular, the present invention relates to a camera for detecting a driver's drowsiness which can increase the number of pixels in an image of a driver's eyes even using an image sensor having the same number of pixels as a conventional camera, instead of a high definition camera. Cameras in accordance with the present invention are, thus, capable of determining whether the driver's eyes are open or closed.

In one aspect, the present invention provides a camera for detecting a driver's drowsiness, the camera comprising: a cylindrical lens mounted in front of the camera, the cylindrical lens configured for enlarging an image in the vertical direction; a convex lens located in the rear of the cylindrical lens; an image sensor for taking an image of a driver's face formed by the cylindrical lens and the convex lens; and an image processor for extracting an eye area from the image of the driver's face and determining whether the driver's eyes are open or closed.

Other aspects and preferred embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein:

FIGS. 3A and 3B are images of a driver's face, in which FIG. 3A is an image taken by a conventional camera and FIG. 3B is an image taken by a camera for detecting a driver's state in accordance with a preferred embodiment of the present invention.

Figure 1:
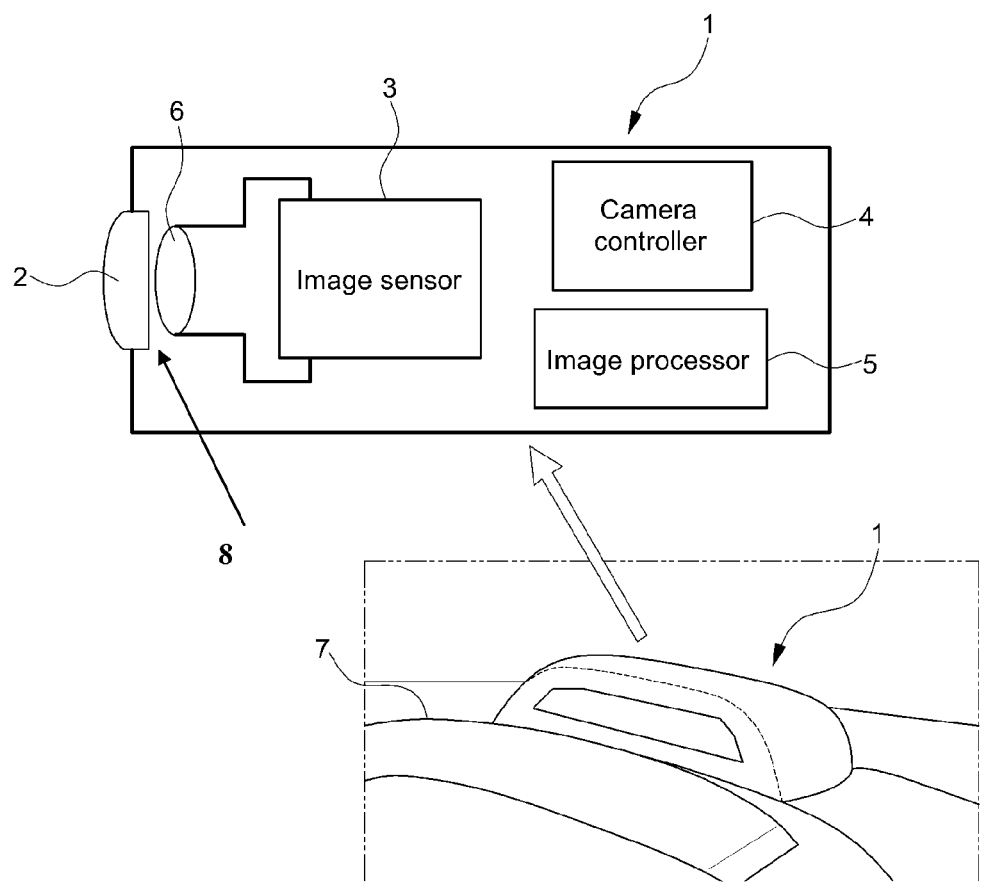
FIG. 1 is a schematic diagram showing the configuration of a camera for detecting a driver's state in accordance with a preferred embodiment of the present invention.

| | |
|---|---|
| Reference numerals set forth in the Drawings includes reference to the following elements as further discussed below: | |
| 1: camera for detecting a driver's drowsiness state | |
| 2: cylindrical lens | 3: image sensor |
| 4: camera controller | 5: image processor |
| 6: convex lens | 7: dashboard |
| 8: rectangular surface | |

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

FIG. 1 is a schematic diagram showing the configuration of a camera for detecting a driver's drowsiness state in accordance with a preferred embodiment of the present invention. As shown in FIG. 1, the camera 1 comprises a cylindrical lens 2 mounted in front of the camera 1, a convex lens 6 located in the rear of the cylindrical lens 2, an image sensor 3, an image processor 5 and a camera controller 4. In particular, the image sensor 3 is configured for taking an image of a driver's face passing through the convex lens 6. The image processor 5 is configured for then extracting an eye area from the image of the driver's face. The camera controller 4 is configured for reading the image captured by the image sensor 3 within a predetermined time, transmitting the read image to the image processor 5, and functioning as a shutter.

The camera 1 for detecting the driver's state according to the present invention may be suitably mounted in/on the vehicle so as to detect a driver's drowsiness state by taking an image of a driver's face. For example, as illustrated in FIG. 1, the camera 1 can be mounted on a dashboard 7 in the front of the driver's vehicle.

Figure 2:
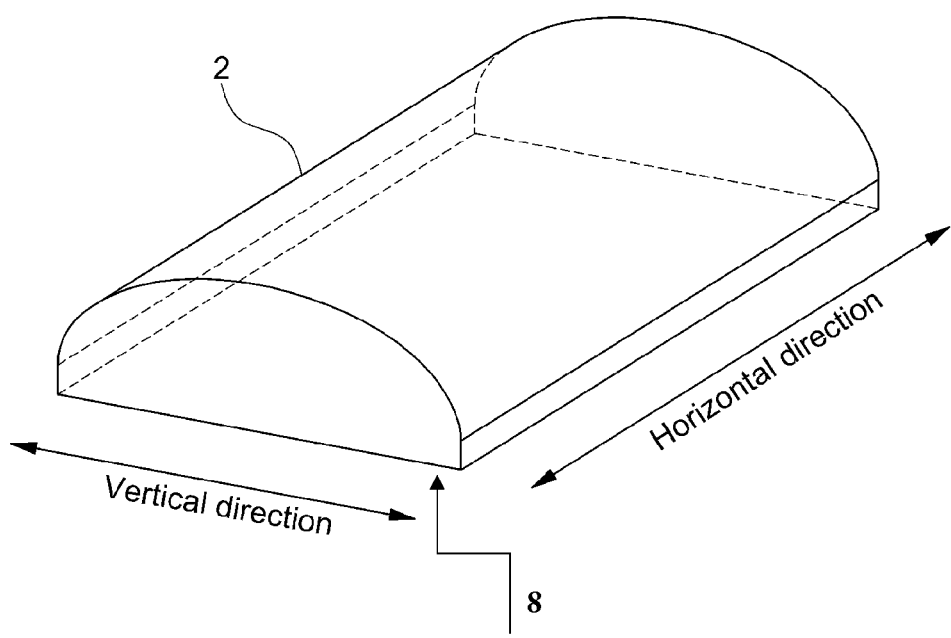
FIG. 2 is a perspective view of a cylindrical lens attached to the camera of FIG. 1.

FIG. 2 is a perspective view of a cylindrical lens 2 attached to the camera of FIG. 1. According to some embodiments of the present invention, the cylindrical lens 2 is configured such that it is possible to obtain an image that is enlarged in the vertical direction, but not enlarged in the horizontal direction. By providing an image that is enlarged in the vertical direction, and preferably not in the horizontal direction, the image processor 5 can easily determine whether the driver's eyes are open. It can further be determined from the position of the iris of the eye whether the driver takes his or her eyes off the road. In accordance with an embodiment of the present invention, for example as shown in FIG. 2, the cylindrical lens 2 can have a rectangular shaped surface 8 (which is shown in FIG. 2 as the bottom surface), and this rectangular shaped surface 8 can be arranged proximal the convex lens 6, for example as shown in FIG. 1. For example, the cylindrical lens 2 can be provided with a rectangular shaped surface 8 that is configured and disposed so as to cover a circular opening of the convex lens 6. In particular, according to some embodiments as shown in FIG. 1, the rectangular shaped surface 8 can be at least as large as the circular opening of the convex lens 6 and can be disposed in front of the entire circular opening of the convex lens 6. Preferably, the surface 8 does not come into contact with the circular opening of the convex lens 6. Of course, the surface 8 can be provided in shapes other than rectangular, and preferably is in any shape that provides an image that is enlarged in the vertical direction. In accordance with the embodiment as shown in FIG. 2, the focus of the cylindrical lens 2 is a straight line along an axis in the horizontal direction, rather than a point.

Figure 3:
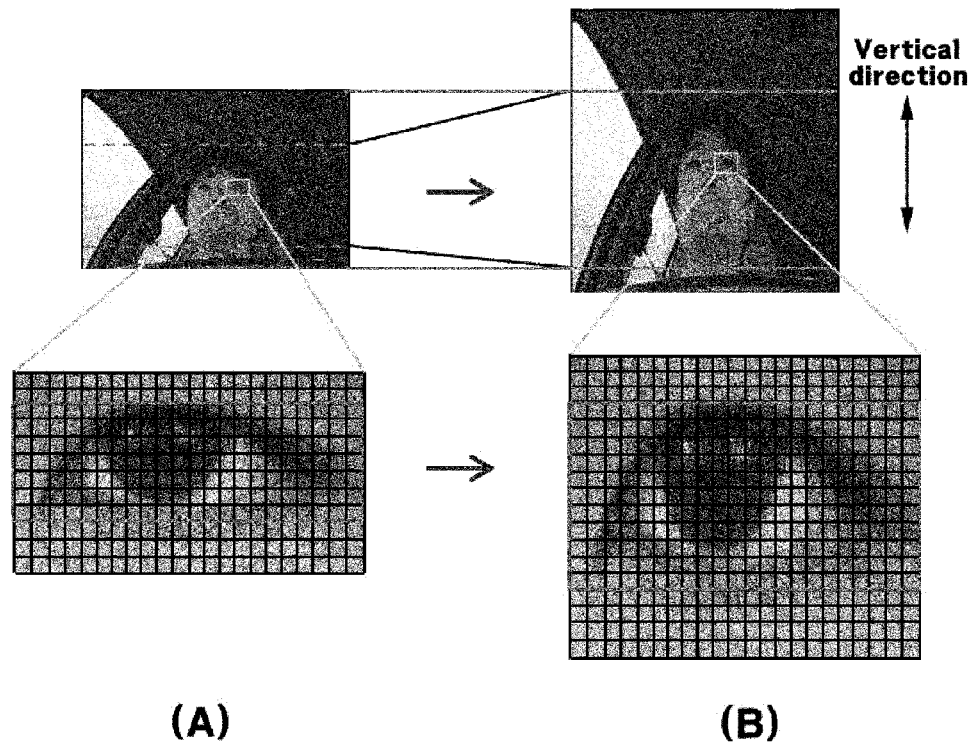
Figure 4:
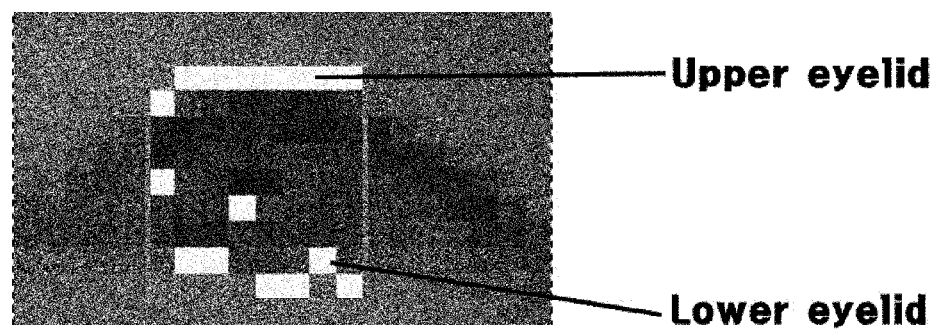
FIG. 4 shows an eye area extracted from an image of a driver's face taken by a conventional camera.

FIGS. 3A and 3B are images of a driver's face, the image of FIG. 3A being taken by a conventional camera. The area between the driver's neck and the upper face is captured by the image sensor 3. The eye area of the face is contained in a square area of 22 pixels in width and 12 pixels in height. In contrast, FIG. 3B is an image taken by the camera 1 for detecting the driver's state according to the present invention. Even in the case of the conventional lens configuration, the image is enlarged by the cylindrical lens 2, and thus the eye area of the face is contained in a larger area of 22 pixels in width and 18 pixels in height. In particular, the number of pixels in the eye area can be increased. Therefore, the camera 1 of the present invention makes it possible to more easily determine whether the driver's eyes are open or closed. While the black and white pixels are clearly seen in the image shown in FIG. 3B, most of the pixels are shown as gray boxes in the image shown in FIG. 4. Therefore, using the conventional lens configuration, it is difficult to distinguish the upper eyelid from the lower eyelid, and it is difficult and often not possible to determine whether the driver's eyes are open or closed.

As described above, according to the present invention, a camera for detecting the driver's state of drowsiness is provided, wherein an image of a driver's face is taken, which is enlarged in the vertical direction by the cylindrical lens.

Moreover, the camera for detecting the driver's state according to the present invention does not require software for enlarging the image, and thus the processing time is relatively short. Further, according to the present invention, once the eye area is extracted, an image enlarged in the vertical direction can be obtained, which facilitates the determination of whether the driver's eyes are open or closed.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A camera for detecting a driver's drowsiness comprising:
   a cylindrical lens mounted at the front of the camera, the cylindrical lens configured for enlarging an image in the vertical direction;
   a convex lens located to the rear of the cylindrical lens;
   an image sensor for taking an image of a driver's face formed by the cylindrical lens and the convex lens; and
   an image processor for extracting an eye area from the image of the driver's face, and determining whether the driver's eyes are open or closed.

2. The camera according to claim 1, wherein the cylindrical lens has a rectangular shaped surface, the rectangular shaped surface being positioned near the convex lens.

* * * * *